United States Patent [19]

Zimmerman et al.

[11] Patent Number: 4,469,671

[45] Date of Patent: Sep. 4, 1984

[54] CONTRACEPTIVE DEVICE

[75] Inventors: Ronald E. Zimmerman, Danville; Philip J. Burck, Indianapolis, both of Ind.; Richard L. Dunn, Birmingham, Ala.

[73] Assignee: Eli Lilly and Company, Indianapolis, Ind.

[21] Appl. No.: 468,436

[22] Filed: Feb. 22, 1983

[51] Int. Cl.³ .......................... A61K 9/00; A61K 9/24
[52] U.S. Cl. ........................................ 424/16; 424/14; 424/19; 424/21; 424/78
[58] Field of Search ................. 424/14, 15, 16, 19–22, 424/28

[56] References Cited

U.S. PATENT DOCUMENTS

| | | | |
|---|---|---|---|
| 3,262,450 | 7/1966 | Elias | 128/270 |
| 3,545,439 | 12/1970 | Duncan | 128/260 |
| 3,639,561 | 2/1972 | Gordon et al. | 424/28 |
| 3,854,480 | 12/1974 | Zaffaroni | 128/260 |
| 3,888,975 | 6/1975 | Ramwell | 424/15 |
| 3,896,819 | 7/1975 | Zaffaroni | 128/130 |
| 3,898,986 | 8/1975 | Zaffaroni | 128/130 |
| 3,916,898 | 11/1975 | Robinson | 128/260 |
| 3,920,805 | 11/1975 | Roseman | 424/15 |
| 3,938,515 | 2/1976 | Leeper et al. | 128/260 |
| 3,946,106 | 3/1976 | Chien et al. | 424/15 |
| 3,967,618 | 7/1976 | Zaffaroni | 128/130 |
| 3,971,367 | 7/1976 | Zaffaroni | 128/130 |
| 3,991,760 | 11/1976 | Drobish et al. | 128/260 |
| 3,992,518 | 11/1976 | Chien et al. | 424/22 |
| 3,993,057 | 11/1976 | Ramwell | 128/130 |
| 3,993,073 | 11/1976 | Zaffaroni | 128/260 |
| 3,995,633 | 12/1976 | Gougeon | 128/260 |
| 3,995,634 | 12/1976 | Drobish | 128/260 |
| 4,012,496 | 3/1977 | Schopflin et al. | 424/15 |
| 4,016,251 | 4/1977 | Higuchi et al. | 424/15 |
| 4,053,580 | 10/1977 | Chien et al. | 424/15 |
| 4,067,961 | 1/1978 | Laughlin | 424/15 |
| 4,069,307 | 1/1978 | Higuchi et al. | 424/22 |
| 4,093,490 | 6/1978 | Ziets et al. | 156/245 |
| 4,144,317 | 3/1979 | Higuchi et al. | 424/21 |
| 4,192,998 | 7/1979 | Gutnick | 424/115 |
| 4,202,880 | 5/1980 | Fildes et al. | 424/78 |
| 4,264,575 | 4/1981 | Zimmerman et al. | 424/22 |
| 4,264,576 | 4/1981 | Zimmerman et al. | 424/22 |
| 4,264,577 | 4/1981 | Zimmerman et al. | 424/22 |

Primary Examiner—Shep K. Rose
Attorney, Agent, or Firm—James L. Rowe; Arthur R. Whale

[57] ABSTRACT

A contraceptive device for intravaginal use comprising a bioinsoluble, biocompatible polyurethane and an acrosin inhibitor.

7 Claims, No Drawings

CONTRACEPTIVE DEVICE

This invention relates to improved devices and compositions useful in human and veterinary medicine for the control of fertility.

BACKGROUND OF THE INVENTION

Contraceptive methods involving the administration of chemical substances are widely practiced among women who desire to limit pregnancies. Such methods control fertility through various biological mechanisms. Among the presently used chemical methods of fertility control, the most important are those which act by means of the following: (a) suppression of ovulation through inhibition of gonadotropin release; (b) alteration of the female reproductive tract to prevent migration of sperm to the site of fertilization or, if fertilization occurs, to block implantation of the zygote (nidation); or (c) spermicidal action.

The oral contraceptives are the most prominent chemical contraceptive agents. These agents are of two types both involving the use of female sex hormones: (a) an estrogen combined with a progestin, and (b) a progestin alone. The contraceptives of the combined type act primarily by suppressing ovulation via negative feedback to prevent gonadotropin (LH and FSH) release by the hypothalamus, but alterations in the reproductive tract may also contribute to the antifertility effect. Such alterations include changes in the cervical mucus (which increase the difficulty of sperm migration) and in the endometrium (which decrease the likelihood of nidation). The action of a progestin alone in a very low oral dose (the "mini-pill") appears to involve primarily alterations in the female reproductive tract, but ovulation suppression may also occur. Although the oral contraceptives are highly effective, their use is associated with unpleasant side effects, including nausea, depression, weight-gain, and headache, plus an increased long-term risk of severe disease such as thromboembolism, stroke, myocardial infarction, hepatic adenoma, gall bladder disease, and hypertension. Bleeding irregularities, e.g., breakthrough bleeding, spotting, and amenorrhea, are also frequent. A progestin, when administered alone, may also cause an increased incidence of changes in menstrual patterns, especially a marked increase in the amount and duration of menstrual bleeding.

Besides the oral route of administration, a progestin alone may be administered systemically by various sustained-release dosage forms which include among other forms: (a) depot injection (IM) of an insoluble progestin (e.g., medroxy progesterone acetate), or (b) subdermal implant. With these methods of administration, the progestin is absorbed into the body continuously at a very low daily dose, and the systemic effects are similar to those produced by oral administration of a progestin. However, as with the oral progestins, since a hormone is still the active agent, these sustained release methods may also cause serious menstrual flow irregularities.

Other chemical methods of contraception include the postcoital administration of estrogens; e.g., diethylstilbestrol or ethynylestradiol. These estrogens act to prevent nidation. Prostaglandins which act as abortifacients are also administered postcoitally. Both of these methods, at present, are limited to emergency situations. Still in the very early stages of development are immunological methods of contraception (vaccination) and methods involving the direct control of LHRH secretion from the pituitary by LHRH agonists or antagonists.

Another group of chemical contraceptive agents in common use are the local spermicides, such as nonoxynol or octoxynol, which are placed in the vagina immediately prior to coitus in the form of creams, foams, jellies, or suppositories containing the spermicide. The spermicidal action takes place either in the vagina or elsewhere in the reproductive tract. For the latter to occur, the spermicidal agent is either adsorbed on sperm membranes or is transported into the uterus under the influence of uterine contractions. The spermicidal methods are not altogether reliable in preventing pregnancy and are inconvenient to use.

The most common alternative to the use of oral contraceptives is the intrauterine device (IUD). Except when composed of copper, the anti-fertility effect of the IUD is not caused by chemical activity. Instead, the material forming the IUD induces a foreign body reaction (irritation) in the contiguous endometrium which appears to interfere in some way with nidation. The use of the IUD is complicated, however, by serious side effects including the possibility of uterine perforation, pelvic inflammation, discomfort, and aggravated menstrual periods.

Many of the above chemical contraceptive agents can be administered via intrauterine or intravaginal devices which pay out the contraceptive at a steady rate for at least 21 days, the average time between menstrual periods in the human female. A recently introduced method of contraception involves the sustained release of progesterone locally within the uterine lumen. In this method, the progesterone is incorporated into a chamber within a flexible intrauterine device (IUD) formed from a polymer which is capable of releasing progesterone continuously into the uterine fluids at a slow rate over a prolonged period of time. The progesterone acts primarily locally to produce progestational alterations in the cervical mucus and endometrium. However, the antifertility action may also be caused by the reaction of the endometrium to the device itself ("IUD effect") or by systemic absorption of progesterone through the uterine membrane. Again, as with other progestin-only therapies, there is an increased incidence of menstrual flow irregularities. Another disadvantage of this contraceptive method, is the increased risk of ectopic pregnancy.

Recently a new device, the flexible IUD bearing metallic copper, has come into widespread use. The contraceptive action of this device results from the combined effects of the copper, which very slowly in the uterine fluids, acting on the blastocyst as well as the cervical mucus or endometrium, and of the IUD itself, which causes a foreign body reaction in the endometrium.

RELEVANT PRIOR ART

Prior art contraceptive devices relevant to this invention which administer the contraceptive agent over a prolonged period of time, can be divided into three general categories: intravaginal devices, polyurethane-based devices and devices which contain surfactants or cationic salts as the contraceptive agent.

Among the intravaginal contraceptive devices are to be found flexible rings composed of a biocompatible polymer containing the contraceptive chemical adsorbed or dissolved in the polymer matrix. One such device is a resilient ring (annular device) capable of being retained in the vagina, consisting of a polymeric matrix containing a progestin as the contraceptive agent—see U.S. Pat. No. 3,545,439. The polymer can be a polysiloxane, dacron, teflon, a polyurethane, polyethylene, rubber, etc.

A second device is described in U.S. Pat. No. 4,202,880 and consists of a cylindrical intravaginal device prepared from 4,4'-diphenylmethane diisocyanate diluted with a mixture of diethyleneglycol, 1,2-propyleneglycol and 1,3-butyleneglycol, and polymerized with a long chain polyol, thus yielding a polyurethane. Medicaments suggested for use in the device cover the entire field of medicine. Abortifacients of the prostaglandin series (as the sodium salts) are among the medicaments specified.

U.S. Pat. No. 3,920,805 discloses a sustained-release device for intravaginal use, comprising an annular medicated core surrounded by a medicated coating. The core and coating are composed of a polysiloxane. The medication is typically a progestational agent although other diverse types of drugs are mentioned.

U.S. Pat. No. 3,916,898 discloses a medicated sponge for intravaginal administration of various hormonal drugs, particularly progestins.

U.S. Pat. Nos. 3,893,880, 4,016,251, 4,069,307 and 4,144,317 disclose a sustained release intravaginal device containing a progestin embedded in an ethylene-vinyl acetate copolymer. U.S. Pat. No. 4,102,998 discloses, among other devices, a sustained release IUD containing progestins or estrogens as the contraceptive drug embedded in a silicone rubber matrix (from vinyl siloxane and other monomer and cross-linking agents). Related U.S. Pat. No. 4,012,496 has a similar disclosure relating to an annular intravaginal device.

Intravaginal and intrauterine devices which are not described as contraceptive devices are set forth in U.S. Pat. No. 3,938,515 which relates to a controlled-release drug formulation, like an intrauterine device, in which a carrier containing a drug in solution is surrounded by a drug-permeable membrane. The carrier may be solid or liquid and may be a polyurethane. Contraceptive drugs are not mentioned.

U.S. Pat. No. 3,262,450 discloses a spongy polyurethane vaginal applicator. Topically applied medicaments for various vaginal disorders (such as trichomonas vaginalis) are used in conjunction with the applicator.

U.S. Pat. No. 4,093,490 describes a vaginal diaphragm made from a thermoplastic elastomer which may be a polyurethane such as an ESTANE.

U.S. Pat. No. 3,639,561 describes, among other devices, a vaginal tampon comprising a prostaglandin abortifacient plus other chemicals (including the trisodium salt of EDTA and the disodium salt of adenosine triphosphate) impregnated in a hydrophilic polyurethane sponge.

Intravaginal devices for controlled release of spermicidal surfactants are disclosed in U.S. Pat. No. 4,067,961, which claim a controlled release device adapted to maintain a useful concentration of a spermicidal nonionic surfactant in micellular form. The surfactant micelles are in turn enclosed in a microporous cellulose membrane through which passes, in a quantity sufficient to maintain a steady-state spermicidal concentration, a spermicidal nonionic surfactant. U.S. Pat. No. 4,031,202 has similar disclosure but the claims are specific to a spermicidal nonionic alkylene oxide surfactant.

U.S. Pat. Nos. 3,995,634, 3,995,633 and 3,991,760 all disclose intravaginal delivery devices of various designs for delivering spermicidally active surfactants, particularly micelle-forming nonionic surfactants. Microporous cellulose forms part of each device. The surfactant is released from such a device in controlled fashion over long periods of time. These devices operate on the same principle as those disclosed in the prior cited patents relating to spermicidal nonionic surfactants.

Additional intrauterine or intravaginal devices for use in contraception are disclosed in the following: U.S. Pat. No. 3,598,122 describes a T-shaped intrauterine device with a liquid core reservoir containing the antifertility agent. The core is surrounded by a membrane permeable to the agent. The core is, illustratively, a polysiloxane containing a progestin dissolved therein. The membrane can be polyethylene, an ethylene-vinyl acetate copolymer or PVP. U.S. Pat. Nos. 3,854,480, 3,896,819, 3,967,618 and 3,993,073 have related, but similar disclosures, being continuation-in-part applications of U.S. Pat. No. 3,598,122.

Bioerodable intrauterine devices are disclosed in U.S. Pat. No. 3,993,057. These devices, in addition to having a geometry such that the retaining arms of the device erodes in a 21 day period, for example, and the remaining reservoir passes out of the body, contain drugs such as prostaglandins and progestational agents as well as many drugs which have no specific hormonal action; i.e., hypnotics, sedatives, etc. Specific examples are limited to intrauterine devices containing oxytocin, progesterone, β-estradiol, and prostaglandins.

U.S. Pat. Nos. 3,898,986 and 3,971,367 (a C-I-P) disclose similar intrauterine devices with female hormones or prostaglandins being specifically illustrated.

U.S. Pat. Nos. 3,946,106, 3,992,518 (a divisional application) and 4,053,580 disclose a silicone polymer matrix containing microsealed drug compartments in which the drug is in a hydrophilic solvent system. This solvent system may have an ionic surfactant as a constituent. The drugs run the ususal gamut from estrogens to diuretics.

U.S. Pat. No. 3,014,987 describes intrauterine and intravaginal devices made from a matrix which is entirely erodable and which releases a drug at a constant ratio. The erodable materials are carboxylic acid polymers and the drugs for the sustained-release device are the usual antifertility agents—the female hormones and prostaglandins—plus many standard pharmaceuticals.

U.S. Pat. No. 3,888,975 discloses a bioerodable device for intrauterine use composed of cross-linked gelatin, with a prostaglandin as the carried drug.

Nonionic surfactant spermicides are also disclosed in U.S. Pat. No. 3,826,757.

Acrosin and/or hyaluronidase inhibiting surfactants for contraceptive use are disclosed in U.S. Pat. Nos. 4,264,575, 4,264,576, and 4,264,577. Intravaginal use of these acrosin inhibitors in a contraceptive method is also disclosed and claimed in U.S. patent application Ser. No. 366,889, filed Apr. 8, 1982. One of the operative intravaginal devices disclosed therein is the subject of this invention.

SUMMARY OF PRIOR ART

Annular intravaginal devices for slow release of various medicaments including contraceptive agents are known. These devices may be made of polyurethane. A particular polyurethane, ESTANE, is known to be biocompatible and has been used in diaphragms. Nonionic surfactants, for use as spermicides, are disclosed as useful drugs in several slow-release intravaginal contraceptive devices. Cationic salts of EDTA and ATP can be present in vaginal tampons composed of a polyurethane sponge. It is known to use acrosin inhibitors as contraceptive agents in the vagina or uterus. However, these prior art references disclose a polysiloxane matrix as a carrier for the particular acrosin inhibitor (all of which to date are surfactant cationic salts) and it has been found that polysiloxane does not release these cationic salts to the vaginal fluids. The release of these cationic surfactant salts from ESTANE is not taught in the prior art.

STATEMENT OF THE INVENTION

This invention provides as a novel article of manufacture, a contraceptive device comprising a bioinsoluble, biocompatible, flexible polyurethane configuration for insertion and retention in the vagina containing an acrosin inhibitor, illustratively an alkyl or alkenyl sulfate or sulfoalkanoate or alkyl sulfate, as a contraceptive agent. It is a characteristic of our novel contraceptive devices that, after an initial wash-out period, the contraceptive agent is delivered to the vaginal fluids at a fixed rate, so as to maintain a fixed contraceptive concentration, depending on the initial loading, over a prolonged period of time, minimally for 21 days, so that during the average 21 day interval between menstrual periods, an effective amount of the contraceptive agent is present in the vaginal fluids, from which it can migrate to the uterus (with sperm), at a steady state concentration. This steady state concentration can be maintained up to 81 days.

The vaginal ring device of this invention is capable of being retentively held in the vagina, and is made from a bioinsoluble, biocompatible (pharmaceutically-acceptable) polyurethane (or other polymer with similar properties) such as the polyether-based polyurethane, sold under the trademark ESTANE 5714. ESTANE 5714 is a strong, soft, resilient elastomer.

As previously stated, the bioinsoluble, biocompatible polymer vaginal ring thus manufactured contains, as a contraceptive agent, an acrosin inhibitor such as an alkyl or alkenyl sulfate salt, an alkyl sulfonate salt or an alkyl or alkenyl sulfoalkylalkanoate salt. The salts have the following formulas.

For alkyl or alkenyl sulfates:

R—OSO$_3$—M     I wherein R is:
(a) $C_{11}$–$C_{30}$ straight chain alkyl or alkenyl;
(b) $C_{10}$–$C_{30}$ branched chain alkyl or alkenyl, the α-carbon of which is not branched; or
(c) $C_{13}$–$C_{30}$ branced chain alkyl or alkenyl, the α-carbon of which is branched.

For alkyl or alkenyl sulfoalkylalkanoate salts:

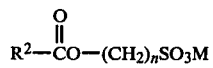
    II wherein $R^2$ is alkenyl or straight chain alkyl of from 9–13 carbon atoms or a branched chain alkyl of from 9–17 carbon atoms, and n is 2, 3 or 4.

For alkylsulfonate salts

R$^1$SO$_3$M     III wherein $R^1$ is straight or branched alkyl of from 11–16 carbon atoms.

In all of the above formulas, M is a pharmaceutically-acceptable, non-toxic cation.

The intravaginal contraceptive devices of this invention, contain, as acrosin inhibitors, cationic salts of various carboxylic and sulfonic, sulfuric, or phosphoric acids of relatively high molecular weight predominately hydrocarbon moieties and the preferred acrosin inhibitors are those illustrated above.

As employed herein and in the claims, the term "α-carbon" denotes the carbon atom of the alkyl or alkenyl group (R, $R^1$, $R^2$) which is bonded to the sulfate or sulfonate or sulfoalkylalkanoate function.

When the "α-carbon" is not branched, a grouping of the following structure is present, using the sulfate function and an alkyl radical for exemplary purposes only, alkyl—CH$_2$—OSO$_3$M When the α-carbon is branched, a grouping of this structure

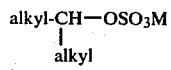

or of this structure

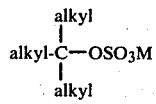

is present.

It will be also understood that when the α-carbon is branched, further branching may occur at other carbon atoms of the alkyl or alkenyl group.

As employed herein and in the claims, the term "alkenyl" means an unsaturated branched chain or straight chain univalent hydrocarbon radical which may contain one or two double bonds. The double bonds may be oriented in either the cis or trans configuration. As will be apparent to one skilled in the art, the double bond cannot be located in the alkenyl chain at either the α-carbon or β-carbon relative to the sulfate, sulfonate or sulfoalkylalkanoate function.

Illustrative alkyl groups which R can represent include: Straight chain alkyl groups of the formula:

CH$_3$(CH$_2$)$_n$— wherein n is an integer from 10 to 29 (preferably 10 to 20); for example:
n-undecyl, n-dodecyl, n-tridecyl, n-tetradecyl, n-pentadecyl,
n-hexadecyl, n-heptadecyl, n-octadecyl,
n-nonadecyl, n-eicosyl, and the like.

α-Branched chain alkyl groups of the formula:

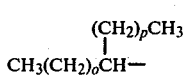

wherein o and p are, independently, integers from 0 to 27, provided that o+p must be no less than 7 and no greater than 27; for example:

$$CH_3(CH_2)_{11}\overset{\overset{\displaystyle CH_3}{|}}{CH}- \quad \text{2-tetradecyl}$$

$$CH_3(CH_2)_9\overset{\overset{\displaystyle (CH_2)_2CH_3}{|}}{CH}- \quad \text{4-tetradecyl}$$

$$CH_3(CH_2)_7\overset{\overset{\displaystyle (CH_2)_4CH_3}{|}}{CH}- \quad \text{6-tetradecyl}$$

$$CH_3(CH_2)_6\overset{\overset{\displaystyle (CH_2)_5CH_3}{|}}{CH}- \quad \text{7-tetradecyl}$$

$$CH_3(CH_2)_8\overset{\overset{\displaystyle (CH_2)_5CH_3}{|}}{CH}- \quad \text{7-hexadecyl}$$

$$CH_3(CH_2)_7\overset{\overset{\displaystyle (CH_2)_6CH_3}{|}}{CH}- \quad \text{8-hexadecyl}$$

$$CH_3(CH_2)_8\overset{\overset{\displaystyle (CH_2)_7CH_3}{|}}{CH}- \quad \text{9-octadecyl.}$$

Alkyl groups not branched at the α-carbon, of the formula:

(a) $CH_3(CH_2)_q\overset{\overset{\displaystyle CH_3}{|}}{CH}(CH_2)_rCH_2-$ wherein r and q are, independently, integers from 0 to 26, provided that r+q must be no less than 6 and no greater than 26; for example:

$$CH_3\overset{\overset{\displaystyle CH_3}{|}}{CH}(CH_2)_{11}- \quad \text{12-methyltridecyl;}$$

(b) $CH_3\overset{\overset{\displaystyle CH_3}{|}}{CH}(CH_2)_a\overset{\overset{\displaystyle CH_3}{|}}{CH}(CH_2)_b-$ wherein a and b are, independently, integers from 1 to 24, provided that a+b must be no less than 5 and no greater than 25; for example:

$$CH_3\overset{\overset{\displaystyle CH_3}{|}}{CH}(CH_2)_3\overset{\overset{\displaystyle CH_3}{|}}{CH}CH_2CH_2 \quad \text{tetrahydrogeranyl;}$$

(c) $CH_3\overset{\overset{\displaystyle CH_3}{|}}{CH}(CH_2)_c\overset{\overset{\displaystyle CH_3}{|}}{CH}(CH_2)_d\overset{\overset{\displaystyle CH_3}{|}}{CH}(CH_2)_e-$ wherein c, d, and e are, independently, integers from 1 to 21, provided that c+d+e must be no greater than 23; for example:

$$CH_3\overset{\overset{\displaystyle CH_3}{|}}{CH}(CH_2)_3\overset{\overset{\displaystyle CH_3}{|}}{CH}(CH_2)_3\overset{\overset{\displaystyle CH_3}{|}}{CH}(CH_2)_2 \quad \text{3,7,11-trimethyldodecyl; or}$$

(d) $CH_3(CH_2)_f\overset{\overset{\displaystyle (CH_2)_gCH_3}{|}}{CH}CH_2-$ wherein f and g are, independently, integers from 0 to 26, provided that g+f must be no less than 6 and no greater than 26; for example:

$$CH_3(CH_2)_q\overset{\overset{\displaystyle (CH_2)_7CH_3}{|}}{CH}CH_2- \quad \text{2-octyldodecyl.}$$

Illustrative alkenyl groups which R represents include: Monounsaturated straight chain alkenyl groups of the formula:

$$CH_3(CH_2)_tCH=CH(CH_2)_sCH_2-$$

wherein t is an integer from 0 to 25 and s is an integer from 1 to 26, provided that t+s must be no less than 7 and no greater than 26; for example:

| | |
|---|---|
| cis-$CH_3(CH_2)_3CH=CH(CH_2)_8-$ | myristoleyl |
| trans-$CH_3(CH_2)_3CH=CH(CH_2)_8-$ | myristeladyl |
| cis-$CH_3(CH_2)_7CH=CH(CH_2)_8-$ | oleyl |
| trans-$CH_3(CH_2)_7CH=CH(CH_2)_8-$ | elaidyl |

Di-unsaturated straight chain alkenyl groups of the formula:

$$CH_3(CH_2)_xCH=CH(CH_2)_yCH=CH-(CH_2)_zCH_2-$$

wherein x is an integer from 0 to 22 and y and z are, independently, each an integer from 1 to 23, provided x+y+z must be no less than 5 and no greater than 24; for example:

| | |
|---|---|
| cis,cis-$CH_3(CH_2)_4CH=CHCH_2CH=CH(CH_2)_8-$ | inoleyl |

Monounsaturated branched chain alkenyl groups of the formula:

$$\overset{\overset{\displaystyle CH_3}{|}}{CH_3CH}-(CH_2)_wCH=CH-(CH_2)_u-CH_2$$

wherein w is an integer from 0 to 23 and u is an integer from 1 to 24, provided that w+u must be no less than 4 and no greater than 24; for example:

$$\overset{\overset{\displaystyle CH_3}{|}}{CH_3CH}CH_2CH=CH(CH_2)_8 \quad \text{3-methyltridec-9-enyl}$$

The alkyl or alkenyl sulfate salts of the formula R—OSO$_3$—M, wherein R and M have the meanings hereinabove defined, are either known compounds, or they can be made from known compounds by known reaction or by modifications thereof obvious to those skilled in the art. Some of the useful acrosin inhibitors are available commercially.

One method for preparing the alkyl or alkenyl sulfates employed in the devices of this invention is by treating the appropriate alkanol or alkenol (R—OH) with chlorosulfonic acid in a non-reactive organic solvent (e.g. hexane or tetrahydrofuran). The reaction can be carried out at room temperature or with mild heating (to about 50°), or it can be carried out at low temperatures (to −25° C.) to prevent side reaction with sensitive starting materials. The product is reacted with a suitable base in order to obtain the particular cation salt which is desired.

Another method for preparing the alkyl or alkenyl sulfate salts is by reacting the appropriate alkanol or alkenol with "pyridine-sulfur trioxide complex" in the presence of pyridine and acetic anhydride in a non-reactive solvent (e.g. toluene). The reaction is carried out, preferably, at an elevated temperature (e.g. 80° to 150° C.). The product of the reaction forms as the pyridinium salt, but other salts can be formed by treating the pyridinium salt with a suitable base, such as potassium hydroxide, sodium hydroxide, lithium hydroxide, calcium hydroxide, magnesium hydroxide, etc.

The $C_{11}$–$C_{16}$ straight chain alkyl group represented by $R^1$ above include the following: undecyl, dodecyl, tridecyl, tetradecyl, pentadecyl, hexadecyl.

The $C_{11}$–$C_{16}$ straight-chain alkyl sulfonates represented by III above are available commercially, usually in the form of their sodium salts. Other salts can be made by processes well known to the art.

The sodium sulfoalkyl alkanoates of Formula II, when n is 3 or 4, are prepared by reacting an appropriate sodium alkanoate ($R^2CO_2Na$) with propane sultone or butane sultone in an inert organic solvent according to the procedure of T. Hikota, *Bulletin of the Chemical Society of Japan*, 43, 2236 (1970). The compounds of Formula II, wherein n is 2, are prepared by treating an alkanoic acid chloride ($R^2COCl$) with sodium isethionate also by the procedure of Hikota supra. The alkanoic acids employed as starting materials, and the sodium salts thereof, are either known compounds or can be prepared from known compounds by methods well known in the art.

Examples of straight chain alkanoate compounds useful for the purpose of this invention are:
sodium sulfopropyl decanoate ($R^2$ is $C_9$ alkyl; n is 3; M is sodium);
sodium sulfopropyl undecanoate ($R^2$ is $C_{10}$ alkyl; n is 3; M is sodium);
sodium sulfopropyl dodecanoate ($R^2$ is $C_{11}$ alkyl; n is 3; M is sodium);
sodium sulfopropyl tridecanoate ($R^2$ is $C_{12}$ alkyl; n is 3; M is sodium); and
sodium sulfopropyl tetradecanoate ($R^2$ is $C_{13}$ alkyl; n is 3; M is sodium);
sodium sulfoethyl dodecanoate ($R^2$ is $C_{11}$ alkyl; n is 2; M is sodium).

When $R^2$ is a branched chain alkyl group, the preferred alkyl groups are those which have the formula:

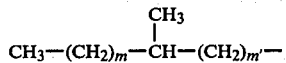

wherein m and m' are, independently, an integer from 0 to 14, provided that m+m' must be no less than 6 or no greater than 14. Examples of branched chain alkanoate compounds useful for the purpose of this invention are:
sodium sulfopropyl 12-methyltridecanoate ($R^2$ is

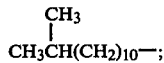

n is 3; M is sodium);
sodium sulfopropyl 15-methylheptadecanoate ($R^2$ is

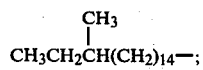

n is 3; M is sodium);
sodium sulfopropyl 16-methylheptadecoanoate ($R^2$ is

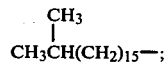

n is 3; M is sodium);

When $R^2$ is an alkenyl group, the preferred alkenyl groups are those of the formula

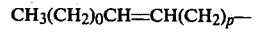

wherein 0 and p are, independently, an integer from 0 to 10, provided that 0+p must be no less than 6 or no greater than 10. Examples of straight chain alkenoate compounds useful for the purpose of this invention are:
sodium sulfopropyl myristoleate ($R^2$ is cis-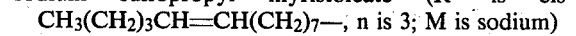, n is 3; M is sodium)
sodium sulfopropyl myristelaidate ($R^2$ is trans-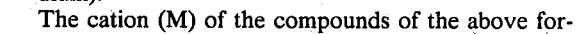; n is 3; M is sodium).

The cation (M) of the compounds of the above formulas (I, II and III) can be any pharmaceutically acceptable, non-toxic cation such as sodium, potassium, lithium, calcium, magnesium, copper, aluminum, pyridinium, substituted pyridinium, zinc, ammonium, or substituted ammonium, e.g. diethanolammonium or triethanolammonium. It will be appreciated by those skilled in the art that when the cation (M) has a valency greater than one, more than one anionic moiety will be associated with the cation.

The alkyl or alkenyl sulfate, sulfonate and sulfoalkylalkanoates salts represented by the above formulas I, II and III control fertility by inhibiting enzymes which are required during fertilization to allow sperm to penetrate the outer investments of the ovum. An ovum contains three outer investments (the cumulus oophorus, the corona radiata, and the zona pellucida) which are barriers to fertilization. In the male, and when first deposited in the female, sperm is incapable of fertilizing an ovum since it lacks the capacity to penetrate the outer investments. Before fertilization can occur, specific hydrolytic enzymes emanating from the sperm must digest each investment so as to form a passage for sperm penetration. The process by which sperm achieve the ability to penetrate the ovum is know as "capacitation". Capacitation involves activation of the ovum penetrating enzymes needed to attack each investment. There is evidence that the activation of the ovum penetrating enzymes may involve the removal of specific inhibitors of the enzymes. The exact biochemical transformations occurring during capacitation are not fully understood, but the enzymes must exert their action either while bound to the sperm membranes or upon release from sperm after the sperm and the ovum make contact in the fallopian tube. For a review of the biochemistry of capacitation and of the inhibition of ovum penetrating enzymes see McRorie et al., *Ann. Rev. Biochem.*, 43, 777 (1974) and E. S. Hafez, Ed., "Human Semen and Fertility Regulation in Men", C.V. Mosby Co., St. Louis, Mo., 1976, pages 201 to 242 and 563 to 582.

It is believed that the alkyl or alkenyl sulfate, sulfonate and sulfoalkylalkanoate salts as used in our novel methods inhibit in vitro the action of hyaluronidase and/or acrosin, the sperm acrosomal enzymes which are known to be responsible in vivo for the penetration of the cumulus oophorus and the zona pellucida, respectfully. Hyaluronidase is a glycosidase which causes degradation of the hyaluronic acid which occurs between the cells of the cumulus oophorus. Acrosin is a proteinase which causes degradation of the glycoproteins of the zona pellucida. Inhibition of each of these enzymes in vivo will lead to interruption of the ovum penetration process thereby effectively preventing fertilization and pregnancy. The inhibition of hyaluronidase (from bull testes) in vitro by $C_{12}$-$C_{14}$ alkyl sulfate sodium salts is described by M. Mathews, *J. Am. Chem. Soc.*, 76, 2948 (1954).

In order to prevent pregnancy, an effective, amount of the alkyl or alkenyl sulfate, sulfonate or sulfoalkylalkanoate salt of Formulas I, II and III must be present at the site of fertilization in the fallopian tube when sperm and the ovum make contact prior to penetration of the ovum. The alkyl or alkenyl sulfate, sulfonate or sulfoalkyl alkanoate salt can be administered by introduction locally within the vaginal cavity. By this mode of administration, the salt is carried to the site of fertilization either by adsorbtion onto sperm membranes or by transport in vaginal fluids. In vaginal fluids, the compound passes to the uterine fluids either adsorbed on sperm membranes or by active transport under the influence of uterine contractions. The preferred method of administration from the standpoint of convenience to the female user is to introduce the alkyl or alkenyl sulfate, sulfonate or sulfoalkylalkanoate salt continously within the vagina during the fertile period of the female (i.e. the period three to four days after ovulation when an ovum is present in the fallopian tube). Thus, an effective amount of the contraceptive agent is present within the vagina each day of the fertile period to prevent fertilization if coitus should occur. Such a contraceptive method is independent of the sex act and avoids the inconvenience of repeated independent dosages.

The continuous administration of the active contraceptive agent can be accomplished effectively by incorporating it into a polyurethane composition and placing said composition retentively in the vaginal cavity. The active compound is slowly introduced into the vaginal fluids by release from the polyurethane at a controlled rate, an effective amount of the compound being present continuously in such fluids. The polyurethane acts as an insoluble, non-irritating carrier matrix for supporting the active compound while it is being introduced into the vaginal fluids. ESTANE is the preferred polyurethane for such use.

The flexible ESTANE rings of this invention containing a contraceptive material comprising a long chain aliphatic sulfate or sulfonate or sulfoalkylalkanoate salt can be prepared by different methods. One convenient procedure is the following, employing sodium n-tetradecylsulfate as the contraceptive agent for exemplary purposes only: A given weight of a segmented polyurethane such as ESTANE 5714 (a polyether based polyurethane manufactured by the B. F. Goodrich Company, Specialty Polymers and Chemical Div., 6100 Oak Tree Boulevard, Cleveland, OH, 44131 and approved for intravaginal use by The Food and Drug Administration) was dissolved in THF. An equal weight of sodium n-tetradecylsulfate was added to form a slurry. The slurry was cast into thin films, each film cut into small pieces and the pieces dried in a vacuum oven at about 70° C. The drug-polyurethane blend pieces were then loaded into the feed section of an injection molding machine (Frohring Mini-jector-Model 45 sold by Newbury Industries, Inc., Newbury, OH) equipped with a mold for a human size vaginal ring (2.244" OD×1.536" I.D. cavity). The drug-polyurethane blend was equilibrated at 130° C. and then forced under pressure into the mold cavities (barrel and nozzle temperatures were also 130° C.). The rings thus produced were annealed by placing over a pipe of slightly smaller diameter (1.5") than the I.D. of the ring to prevent shrinkage. Annealing was carried out in an air-circulating oven at 45° C. for 30 minutes.

The molded rings were coated with ESTANE or similar polymer by dipping repeatedly in a DMF solution containing 12% (w/w) ESTANE 5714. Solvent was allowed to evaporate for 1 hour between dips. Coated rings were prepared with the ratio of radius of the coated ring to the ring itself varying from 1.02 to 3.29. Studies of drug release rates indicated that thinner coatings (ratio 1.02-1.06) yielded the desired drug delivery rate.

Rings capable of being retained in the vagina for continuous release prepared as above, but lacking a coating, give large initial bursts of drug when first placed in contact with vaginal fluids. With a coating such as specified above, however, the drug release initially is below that required for successful contraception. Coated rings, therefore, must be equilibrated, for example, in water for periods up to three weeks (depending on the thickness of the coating), while the contraceptive salt migrates from the body of the ring into the coating in sufficient quantity to insure the presence of an effective steady-state level of the contraceptive agent in the vaginal fluid. Alternatively, and preferably, the manufactured ring is held at room temperature or higher for three weeks, during which time the contraceptive salt again migrates from the core into the coating.

Vaginal rings prepared as above release the contraceptive agent into the vaginal fluids at a constant rate sufficient to provide a contraceptive concentration of the drug for 21 days or more.

Although the vaginal device prepared as above contained 50% acrosin inhibitor, similar devices containing 18-25% drug were prepared in similar fashion, and gave constant drug release.

Vaginal rings of a size suitable for insertion into rabbit vaginas were prepared as above with the cavities in the injection molds being, 0.878" O.D.×0.473" I.D. These rings were coated without annealing with 100-150μ layers of ESTANE 5714.

In vivo testing of rings thus fabricated in rabbits was carried out as follows: a ring as manufacture was equilibrated in 50 ml. of water at 37° C. and assayed 2-3 times daily for release of sodium n-tetradecylsulfate. When the release rate exceeded 500/mcg./day, the rings were sutured into the vaginas of five Dutch belted does. After recovery from surgery, the does were bred to bucks of proven fertility weekly for four weeks. Ten days after the last breeding, the does were sacrificed and their uteri examined for embryos. None of the does became pregnant.

In a similar test, blank ESTANE rings, water-equilibrated (19 days, 37° C.), blank ESTANE rings and ESTANE rings containing water-equilibrated 50% sodium n-tetradecyl sulfate with a release rate of >400 mcg./day were made. The rings were again surgically implanted into female rabbits. The rabbits containing blank rings were bred once to fertile bucks while those containing test rings were bred weekly for 4 weeks to the same males. The following data were obtained:

| Number of Animals | Treatment | Number of Embryos | Number of Ovulations | Percent Pregnancy |
|---|---|---|---|---|
| 5 | Blank Ring | 22 | 39 | 100 |
| 5 | Blank Ring* Water Extracted | 24 | 39 | 100 |
| 15 | Ring Containing sodium n-tetradecyl-sulfate | 0 | 175 | 0 |

It is desirable that the rate of delivery of the active contraceptive agent—the acrosin inhibitor—be substantially constant over the period in which the carrier composition is present in the vaginal cavity. Preferably, the duration of drug delivery should cover the fertile period of the female. Thus, the duration of release should be ideally about one month. The carrier composition can then be removed at the start of the menstrual period and re-inserted after bleeding stops. However, as long as an effective amount of the active compound can be released into the vaginal fluids, intravaginal composition can be inserted prior to coitus and removed shortly thereafter, rather than allowing the composition to be retained in the vagina for a longer duration of time.

Release rates of from 0.5 to 10 mg. of contraceptive sulfonate, sulfate or sulfoalkyl alkanoates salts per day maintained a contraceptive release rate of >400 mcg./day of sodium tetradecylsulfate for 61 days. Such release rates are desirable when utilizing intravaginal devices such as that illustrated above.

We claim:

1. A flexible contraceptive device capable of being held retentively in the vagina comprising a bioinsoluble, biocompatible polyurethane core permeated with a cationic salt acrosin inhibitor, said core being coated with a thin polyurethane film, and capable of releasing to the vaginal fluids a contraceptive concentration in excess of 400 mcg./day of said cationic salt acrosin inhibitor for 21 days or longer.

2. A contraceptive device according to claim 1 in which the polyurethane is an ESTANE.

3. A contraceptive device according to claim 1 in which the acrosin inhibitor is a cationic salt of an alkyl or alkenyl sulfate, an alkyl sulfonate or an alkyl or alkenyl sulfoalkyl alkanoate.

4. An intravaginal contraceptive device according to claim 3 in which the acrosin inhibitor is an alkyl or alkyl sulfate salt of the formula:

$$R-OSO_3-M$$

wherein R is:
$C_{11}-C_{30}$ straight chain alkyl or alkenyl;
$C_{10}-C_{30}$ branched chain alkyl or alkenyl, the α-carbon of which is not branched; or
$C_{13}-C_{30}$ branched chain alkyl or alkenyl, the α-carbon of which is branched, and M is a pharmaceutically-acceptable, nontoxic cation.

5. An intravaginal contraceptive device according to claim 3 in which the acrosin inhibitor is an alkyl or alkenyl sulfoalkyl alkanoate salt of the formula $$R^2-\overset{O}{\underset{\|}{C}}O-(CH_2)_nSO_3M$$

wherein $R^2$ is alkenyl or straight chain alkyl of from 9-13 carbon atoms or a branched chain alkyl of from 9-17 carbon atoms, n is 2, 3 or 4, and M is a pharmaceutically-acceptable, non-toxic cation.

6. An intravaginal contraceptive device according to claim 3 in which the acrosin inhibitor is an alkylsulfonate salt of the formula $$R^1SO_3M$$

wherein $R^1$ is straight or branched alkyl of from 11-16 carbon atoms, and M is a pharmaceutically acceptable non-toxic cation.

7. An intravaginal contraceptive device according to claim 4 in which the acrosin inhibitor is sodium n-tetradecyl sulfate.

* * * * *